US007390673B2

(12) United States Patent
Klimant et al.

(10) Patent No.: US 7,390,673 B2
(45) Date of Patent: Jun. 24, 2008

(54) METHOD AND DEVICE FOR IDENTIFYING VOLATILE SUBSTANCES IN SOLUTION

(75) Inventors: Ingo Klimant, Mintraching (DE); Achim Stangelmayer, Neuburg a.d. Donau (DE)

(73) Assignee: Merck Patent GmbH, Darmstadt (DE)

( * ) Notice: Subject to any disclaimer, the term of this patent is extended or adjusted under 35 U.S.C. 154(b) by 705 days.

(21) Appl. No.: 10/476,639

(22) PCT Filed: Apr. 8, 2002

(86) PCT No.: PCT/EP02/03868

§ 371 (c)(1),
(2), (4) Date: Nov. 4, 2003

(87) PCT Pub. No.: WO02/090975

PCT Pub. Date: Nov. 14, 2002

(65) Prior Publication Data

US 2004/0136874 A1    Jul. 15, 2004

(30) Foreign Application Priority Data

May 5, 2001  (DE)  ................. 101 21 999

(51) Int. Cl.
*B01L 3/00*   (2006.01)
*G01N 7/00*   (2006.01)
*G01N 21/76*  (2006.01)
*G01N 1/22*   (2006.01)
*G01N 1/18*   (2006.01)
*B01D 63/00*  (2006.01)

(52) U.S. Cl. ............................ 436/177; 422/83; 422/99; 422/52; 422/102; 210/321.75; 436/181

(58) Field of Classification Search ................. 422/102, 422/83, 99, 52; 210/321.75; 436/177, 181
See application file for complete search history.

(56) References Cited

U.S. PATENT DOCUMENTS

| 3,632,476 A | * | 1/1972 | Fried .......................... 435/144 |
| 5,256,604 A | * | 10/1993 | Aitken ......................... 501/45 |
| 5,494,640 A | | 2/1996 | Simon et al. |
| 5,633,169 A | | 5/1997 | Young et al. |

(Continued)

FOREIGN PATENT DOCUMENTS

CH             649383         5/1985

(Continued)

OTHER PUBLICATIONS

Luebbers D W et al: "Quantitative Fluorescence Photometry With Biological Fluids and Gases" Advances in Experimental Medicine and Biology, Spring St., NY, US Bd. 75, 1976, Seiten 65-68, XP000566843.

*Primary Examiner*—Jill Warden
*Assistant Examiner*—Lore Ramillano
(74) *Attorney, Agent, or Firm*—Millen, White, Zelano, Branigan, P.C.

(57) ABSTRACT

The invention relates to a method for fluorimetrically or photometrically identifying gaseous substances or substances, which can be converted into a gaseous state, in samples. Decomposition reactions, optional purification steps, and detection can be carried out in a cell, which comprises one or more ion-permeable membranes, in a user-friendly and selective manner without losing any substances.

16 Claims, 4 Drawing Sheets

U.S. PATENT DOCUMENTS 5,733,777 A * 3/1998 Dudney .................. 435/304.1
6,602,414 B2 * 8/2003 Warner .................. 210/321.75
6,740,294 B2 * 5/2004 Radmacher et al. ........... 422/83

FOREIGN PATENT DOCUMENTS

| DE | 1817312 | 8/1969 |
|----|---------|--------|
| EP | 0663239 | 7/1995 |
| EP | 0930368 | 7/1999 |
| WO | WO0075653 A2 * | 12/2000 |

* cited by examiner

METHOD AND DEVICE FOR IDENTIFYING VOLATILE SUBSTANCES IN SOLUTION

The invention relates to a method and an apparatus for the photometric or fluorimetric determination of volatile substances in solution.

For certain analytical problems, individual components are separated from the sample mixture by conversion into the gas phase. These gaseous components can then be determined by means of gas chromatography, atomic absorption, IR or chemiluminescence spectroscopy or by means of indirect methods, such as conductometry, coulometry, potentiometry, gas volumetric analysis, acidimetric titration, manometric measurement, iodometric titration, fluorimetry or photometry.

For certain problems, special methods have been developed, such as, for example, in U.S. Pat. No. 4,201,548, which describes a method for the determination of volatile substances in liquids in which the sample is introduced into a plastic container which is delimited by a semipermeable membrane. After passing through the membrane, the analyte colours a support membrane impregnated with indicator. However, this apparatus for visual detection is not suitable for photometric or fluorimetric detection.

U.S. Pat. No. 5,275,956 describes the determination of organic chlorine-containing compounds by chemiluminescence. The apparatus used contains a digestion zone (oxidation zone), a reaction zone in which the chemiluminescent compound is formed, and a detection zone. The very complex apparatus is furthermore provided with connectors, pumps and detectors.

This gives rise firstly to the object of developing an extremely simple, universal test system which allows various substances from a very wide variety of samples to be determined by photometric or fluorimetric analysis.

A first approach in this respect was developed in EP 0 663 239, which describes a test kit for the chemical analysis of gaseous sample constituents. The kit contains an apparatus consisting of two individual containers. One container serves for accommodation of the sample and liberation of the gas, the other for detection. The gas is transferred from the first container to the second container via an adapter. The disadvantage of the kit is the need to use two containers and to connect these via an adapter during use. This requires high experimental complexity. In addition, excessively slow connection of the two containers entails the risk of escape or ingress of gas. The analytical data can thus easily be incorrect.

The object of the present invention is therefore to provide a method and an apparatus for fluorimetric or photometric determination which enable:

a broad range of samples to be analysed for various gaseous substances or substances which can be converted into the gas phase, the method to be carried out with low equipment and experimental complexity, a very selective and sensitive analysis to be carried out.

It has been found that both the selectivity and sensitivity as well as the experimental complexity of the determination of volatile substances in samples can be greatly improved if digestion and detection take place in a single container.

The container, for example a cell, is to this end divided into at least two reaction zones by a gas-permeable membrane. After addition of the sample substance and further necessary reagents, the container is closed. All further analytical steps, such as digestion, purification and detection, can be carried out in the closed container.

The invention therefore relates to a cell for the photometric or fluorimetric determination of volatile substances in samples, characterised in that the cell is divided by an ion-impermeable, gas-permeable membrane into two zones in which, separated by the membrane, a compartment for sample and digestion solution (3) and a compartment for indicator solution (1) which is filled with indicator solution are located, and the cell can be sealed in a gas- and liquid-tight manner by at least one closure (5).

The invention also relates to a cell for the photometric or fluorimetric determination of volatile substances in samples, characterised in that the cell is divided by at least two gas-permeable membranes (22, 24) into at least three zones in which, separated by the membranes, a compartment for sample and digestion solution (25), a compartment for washing solutions (23) which is filled with washing solution, and a compartment for indicator solution (21) which is filled with indicator solution are located, and the cell can be sealed in a gas- and liquid-tight manner by a closure (27).

In a preferred embodiment, at least one membrane, preferably all membranes, of the cells according to the invention consists of a silicone polymer.

In a further preferred embodiment, at least one membrane, preferably all the membranes, have been clamped into the cell.

In another preferred embodiment, at least one membrane, preferably all the membranes, have been polymerised into the cell.

The invention also relates to an analysis kit for the determination of gaseous substances or substances which can be converted into the gas form in samples, which contains at least one cell according to the invention which a) is divided into at least two sub-zones by at least one hydrophobic, semipermeable membrane,
b) contains the indicator solution in the lower sub-zone,
c) contains washing solutions in optional central sub-zones,
d) can be filled with the sample and optional ancillary reagents in the upper sub-zone,
e) has a gas- and liquid-tight closure.

The invention furthermore relates to a method for the determination of volatile substances in samples using a cell according to the invention, in which a) the cell is opened,
b) filled with the sample and optional ancillary reagents in the upper sub-zone,
c) sealed by means of the closure,
d) the cell is inverted,
e) the sample is digested,
f) the cell is re-inverted,
g) the indicator solution is measured.

Figure 1:
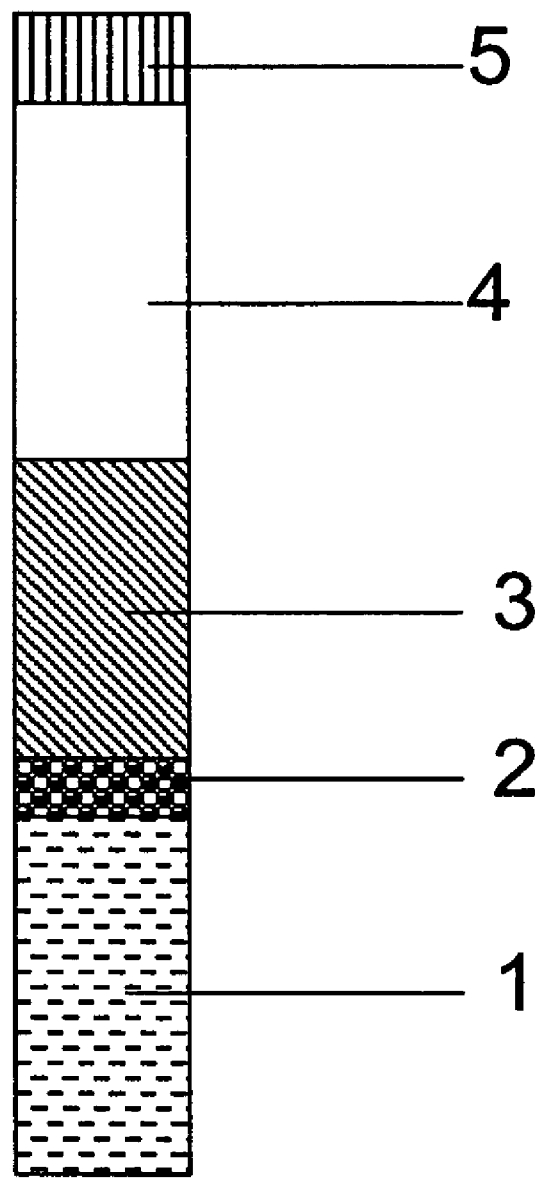
FIG. 1 depicts a cell according to the invention.

The method according to the invention is suitable for the determination of a very wide variety of analytes, such as, for example, gaseous compounds which can be determined with or without prior conversion, volatile organic compounds, such as phenols or halogenated hydrocarbons, or compounds which are determined by a chemical reaction involving gas evolution which is carried out in advance in the digestion part of the cell, such as nitrate, which is converted into $NO_x$.

Examples are shown in the following table:

| Substance to be determined | Analyte |
|---|---|
| Total organic carbon (TOC) | $CO_2$ |
| Total inorganic carbon (TIC) | $CO_2$ |
| $NH_4^+$ | $NH_3$ |
| $CN^-$ | HCN |
| Hypochlorite | $Cl_2$ |
| $S^{2-}$ | $H_2S$ |
| $NO_3^-$ | $NO_x$ |
| $HSO_3^-$ | $SO_2$ |
| CHCs | |
| Volatile amines | |
| Non-volatile quaternary ammonium ions (via Hoffmeister elimination) | |
| Tetramethylmercury | |
| Heavy metals (indirect) | |

The method according to the invention is based on the use of a container into which can be introduced firstly the indicator solution and secondly the sample solution with the digestion reagent. A membrane provides for separation of the two zones.

To this end, firstly the indicator solution is introduced into the container, and the membrane is subsequently introduced. The membrane can then optionally be covered with the digestion solution. After addition of the sample, the container is closed.

Thus, all reagents required for the analysis are located in a single container. This concept enables simple and user-friendly analysis of the samples. The working instructions for the analysis are restricted to the following steps:
1. unscrewing of the closure from the container
2. introduction of the sample by pipette
3. screwing-on of the closure
4. inversion
5. digestion
6. inversion
7. measurement The container or the analytical apparatus is preferably made of glass or of another material, for example an organic polymer, preferably optically transparent or at least provided with a window of optically transparent material. The container or the analytical apparatus preferably consists of materials which are used for the production of photometer cells, such as, for example, polycarbonate and particularly preferably quartz.

Since the container is inverted during the analysis, it contains a liquid- and gas-tight closure in the form of a screw cap or stopper. In its preferred embodiment, the container is designed in such a way that it can be inserted, for example, into a standard commercial dry thermostat for digestion of the sample and can be inserted as measurement container into a standard measuring instrument for detection. For photometric or fluorimetric analytical methods, the design as cell is therefore preferred. This cell can have a circular, square or rectangular shape. The container according to the invention is hereinafter referred to as cell.

For the purposes of the invention, the term photometric or fluorimetric determination also includes turbidity measurement, for example nephelometry.

In order to separate the digestion zone from the detection zone (indicator solution zone), a gas-permeable and ion-impermeable membrane is introduced into the cell. This membrane is impermeable to liquids or ions, in particular protons, and permeable to gases. It forms a mechanically stable separation which is in close contact with the cell wall.

The membrane preferably has the following additional features:
temperature-stability
mechanical stability (pressure and tension)
uniform layer thickness
good adhesion to the wall of the cell
decomposition stability to strong bases.

The membrane should furthermore be free from carbon-containing elimination products which falsify the analysis of carbon or other elimination products which influence the indicator solution.

These requirements are satisfied by hydrophobic, porous, gas-permeable and combination membranes comprising silicone and Teflon membranes.

The membrane can be introduced into the cell in various ways. For example, it can be attached to the inner wall of the cell by adhesive bonding (for example directly or in a gap or on a projection), clamping (for example directly or through insertion of a moulding) or polymerisation.

Preferred ways of introducing the membrane are explained in greater detail below:

Polymerisation of the Membrane:

For introduction by polymerisation, the membrane or the membrane constituents should also have the following properties:
ability to float on aqueous solutions
polymerisability on an indicator solution buffered at strongly basic pH Particularly suitable membranes are those which can be produced in relatively short polymerisation times.

In a typical procedure, the indicator solution is firstly introduced into the container. A silicone membrane is then formed on the indicator solution by dropwise addition of a silicone prepolymer. The liquid silicone prepolymer floats on the indicator solution and forms a uniform film. After polymerisation, the silicone film forms a hydrophobic, gas-permeable, ion-impermeable membrane which is firmly attached to the container wall.

In the production of silicone membranes, a distinction should be made between two types of starting material: condensation-polymerising silicones and addition-crosslinking silicones.

Whereas condensation-polymerising silicones are distinguished by easy processability of the prepolymers and good adhesion to the glass wall of the container, their use is not possible for some applications since they often contain residues of solvents or carbon-containing elimination products. For this reason, addition-crosslinking silicones are preferably used for the apparatus according to the invention.

In contrast to the condensation-crosslinking silicones, these can only react to a limited extent with the hydroxyl groups of the glass wall. The glass wall is therefore preferably partly or fully hydrophobicised in advance. This priming of the glass wall prevents the formation of a strongly curved meniscus of the liquid surface and thus guarantees a sufficiently large contact area of the silicone with the glass wall. The hydrophobicisation of the glass wall is carried out by covalent coupling of, for example, trimethoxysilane (T9895, ABCR GmbH & Co) or propyltrimethoxysilane or by coating the glass wall with a thin silicone layer.

Preference is also given to the use of glass containers having a hydrophobic inner wall.

Starting materials for the production of silicone membranes are known to the person skilled in the art. Typically, a copolymer is prepared from a linear chain-form component (base) with reactive end groups and a branched component (crosslinker) with reactive end groups. The reaction initiators for the chemical reaction which results in crosslinking are, depending on the nature of the base and crosslinker, various chemicals or alternatively physical parameters (pressure change, temperature change). In the case of condensation-crosslinking silicone prepolymers, this is usually water in the form of the water vapour content in the air, while in the case of addition-crosslinking silicone prepolymers it is usually a chemical, a so-called free-radical initiator.

Adhesive Bonding of the Membrane:

A further preferred embodiment is the adhesive bonding of a prefabricated membrane or a membrane-coated membrane support into the container. For example, prefabricated membranes made from gas-permeable plastics, preferably Teflon or other gas-permeable materials, can be bonded to the cell wall by means of an adhesive step. The adhesives used should not contain any interfering substances and should be stable in the solvents of the solutions employed.

The adhesives used should not contain any substances which interfere with the determination reaction, such as, for example, solvents (acetone, toluene or ethanol), which liberate carbon-containing constituents during the preparation and processing of the adhesive or during the later digestion reaction and thus influence the determination reaction. Furthermore, the adhesives should be stable in the solvents of the solutions employed. A suitable adhesive for adhesive bonding of silicone membranes into the cell is, for example, a two-component addition-crosslinking hydrogen-eliminating silicone, such as, for example, Kwik-Sil® low viscosity silicone kit, marketed by World Precision Instruments, Inc.

Figure 4:
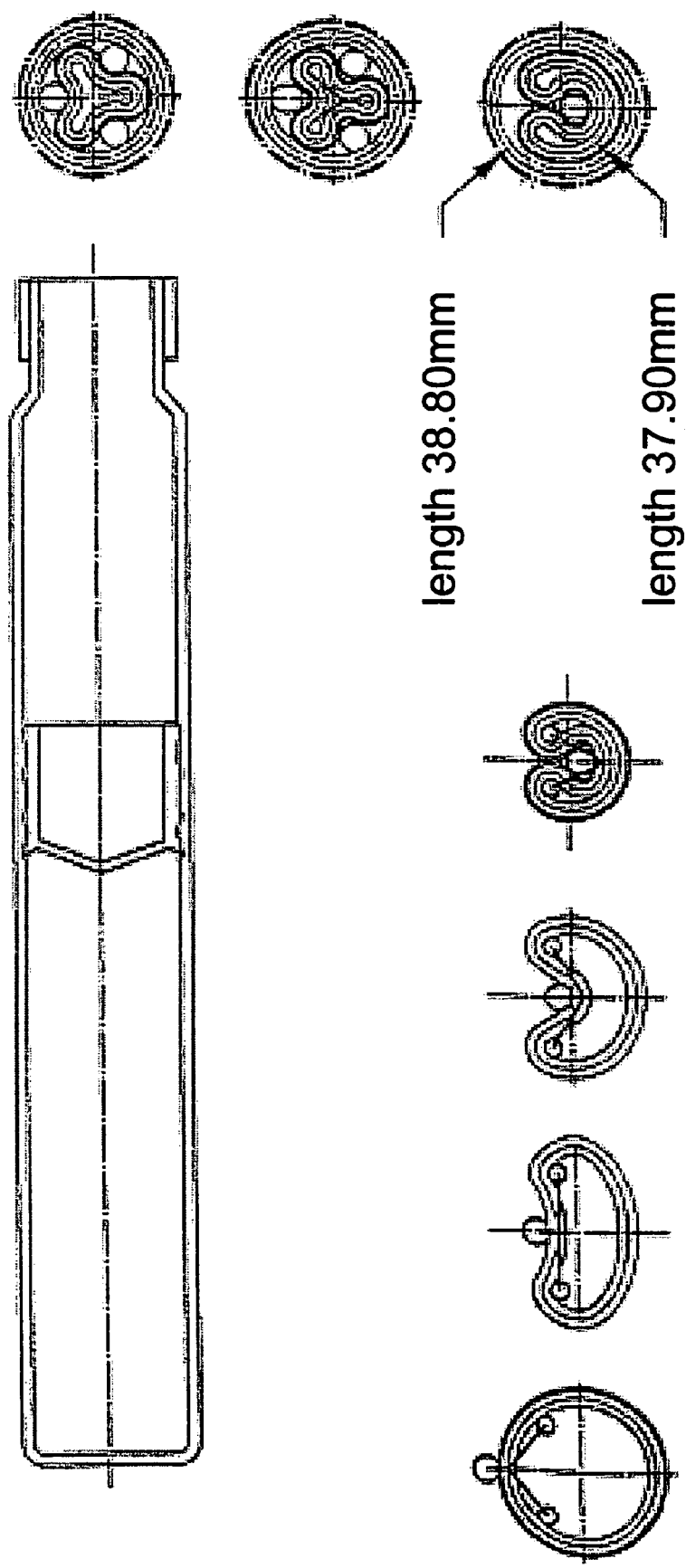
FIG. 4 shows a moulding having an integrated gas-permeable, ion-impermeable membrane which, due to its shape, can be spread out into the container.

Clamping of the Membrane:

A further preferred embodiment is the introduction of a moulding with an integrated gas-permeable, ion-impermeable membrane which spreads out into the container due to its shape. The moulding can consist, for example, of silicone. The moulding preferably has a technical design such that it automatically springs up in a similar manner to a compressed rubber ball and thus spreads out into the container. A moulding of this type is described in FIG. 4, which shows the folded moulding (top), the unfolding of the moulding (bottom right) and the unfolded moulding located in the cell (bottom left).

In a preferred embodiment, the membrane for clamping into the cell consists of a silicone polymer which is foldable. In this way, it can be introduced into the cell and then unfolds in such a way that it fits precisely in the cell in a leak-proof manner.

Accordingly, a cell according to the invention with clamped-in separation membrane is produced by
provision of a suitable cell,
introduction of the indicator solution,
insertion of the folded membrane with the aid of a tool,
precise positioning of the membrane in the final position above the liquid level of the indicator solution,
release of the tool and thus unfolding and spreading-out of the membrane into the cell
optionally introduction of a digestion solution
sealing of the cell with a closure cap.

The membrane itself can in all embodiments consist of one or more components.

If the analysis container is to be divided into only two sub-zones, the sample or digestion solution can be introduced into the upper sub-zone after introduction of the membrane.

If volatile components which interfere with an analysis are to be expected in addition to the analyte, firstly washing solutions can be introduced onto the separation membrane and covered with a second membrane. The cell is thus divided into more than two, preferably three, sub-zones. This arrangement is appropriate, for example, in a TOC test in the presence of hydrogen sulfide. A further sub-zone which contains lead (II) nitrate solution as washing solution is divided off by a second membrane between the indicator solution and sample or digestion solution. The digestion causes both $CO_2$ and $H_2S$ to enter the gas phase and pass through the first membrane. Whereas the interfering $H_2S$ is retained by the washing solution, the $CO_2$ passes through the second membrane into the indicator solution, where it achieves a colour change.

Independently of the way in which the cell is divided or whether an additional sub-zone with washing solution is present in the container, the sample solution and optionally a digestion solution are introduced into the uppermost sub-zone.

In this uppermost digestion sub-zone, either the substance to be analysed is converted into a volatile form or a reaction is carried out which liberates a volatile substance which serves as indirect determination of the analyte. This can be carried out with or without addition of a particular digestion solution. Whereas a digestion solution is used for the determination of $CO_2$ or $NH_3$, this is not necessary for the determination of, for example, volatile hydrocarbons.

With the aid of a suitable digestion solution, certain substances can be converted selectively into the gas phase. For example, weak acids or gases thereof can be expelled using a pH 4 buffer, but strong acids cannot. In addition, the creation of temperature gradients within the cell during the digestion, for example by heating the digestion zone only selectively, allows the gas formed to be transported preferentially into the colder indicator sub-zone.

A further possibility for enriching the analyte in the indicator part consists in the use of different volumes for indicator volume and sample volume. If the volume of the sample solution is larger than that of the indicator solution, the gas formed is in higher concentration in the indicator solution.

Although the detection of the analyte using the indicator solution represents the final step of the method according to the invention, the indicator solution is all introduced into the analysis container at the beginning. Only after introduction of the indicator solution can the first separation membrane be applied to the solution or installed above the solution.

The indicator solution can be an aqueous or organic system or a mixture of the two. The indicators can be chromophoric or fluorophoric systems. Equally, however, the inherent colour or inherent fluorescence of the analytes can also be detected. In this case, the indicator solution serves only as solvent for the gaseous component. Through variation of the indicator, the buffer capacity of the solution, the pH or the addition of complexing agents, the selectivity of the indicator solution can be varied in accordance with the analyte to be detected. For example, a colour change, fluorescence intensity or fluorescence life can be detected.

The analysis container according to the invention is, due to its simple construction, particularly for use in analysis kits. In this case too, the shape of the container should be suitable for direct insertion into thermostats or photometers or other analytical instruments. The use of a cell is therefore preferred.

The cell present in the analysis kit is filled with the respective indicator solution, and the indicator sub-zone is delimited from the digestion zone by means of a membrane. If further purification of the analyte by means of washing solution is necessary for the intended analysis, the washing solution is firstly introduced onto the first membrane, and a further membrane is subsequently applied in order to separate off the digestion zone. Whether the digestion solution is already stored in the cell before the analysis is carried out depends on its stability. In one case, the digestion solution has already been introduced into the cell, so that it is merely necessary to add the sample solution in order to carry out the analysis. If no digestion solution is necessary or the digestion solution is stored separately for stability reasons, both sample and also optionally the digestion solution must be added when carrying out the analysis. After the cell has been filled with all requisite components, it is sealed in a liquid- and gas-tight manner and subjected to the method according to the invention.

In this way, it is possible to carry out very selective analyses without major experimental complexity. The optional further purification by means of a washing solution also enables contaminated actual samples or samples with interfering components to be measured. Enrichment or purification of the sample before introduction into the analysis container is not necessary. The closed system enables very sensitive measurements to be carried out without loss of analyte.

FIG. 1 depicts a container according to the invention. Sub-zone (1) contains the indicator solution. This is separated from the digestion solution in sub-zone (3) by the semipermeable membrane (2). The digestion solution preferably does not occupy the entire sub-zone (1), but instead leaves a gas space (4) free. The free gas space in the cell is necessary for pressure equalisation. The cell is sealed by means of a closure (5).

Figure 2:
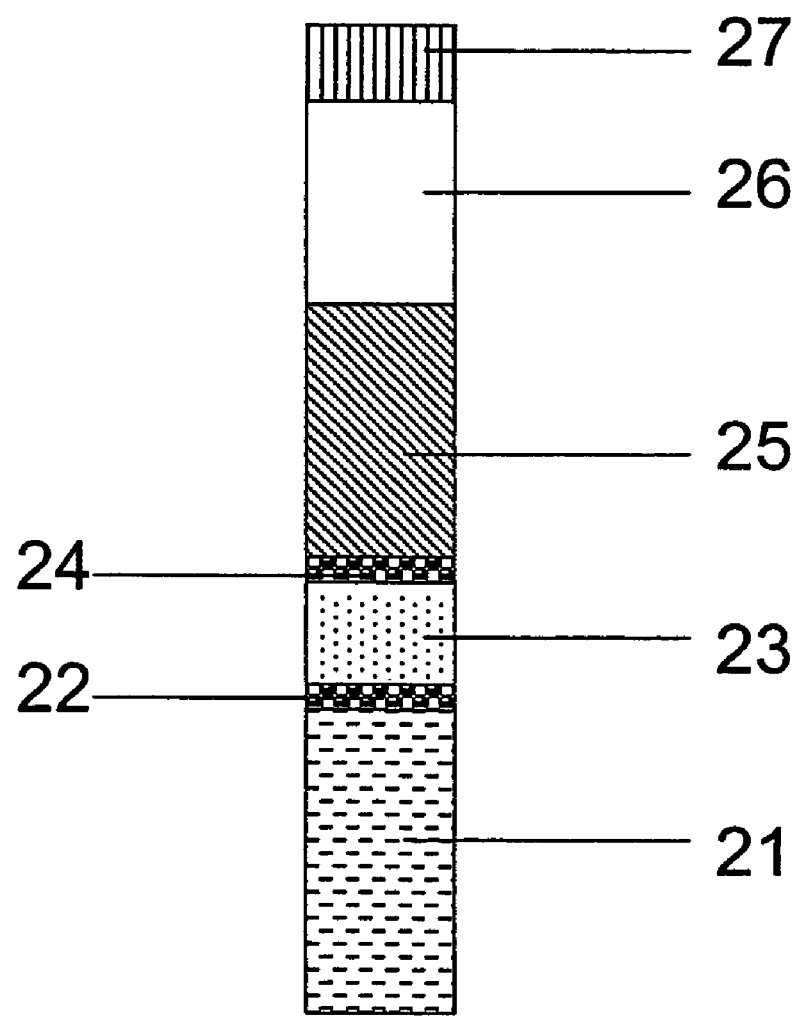
FIG. 2 shows an analysis container according to the invention having an additional sub-zone for washing solutions.

In FIG. 2, the indicator solution (21) is delimited by an ion-impermeable, gas-permeable membrane (22). This is followed by a washing solution (23), which is covered by a further membrane (24). The digestion solution (25) and the gas space (26) are located above this membrane. The cell is sealed by means of a closure (27).

Figure 3:
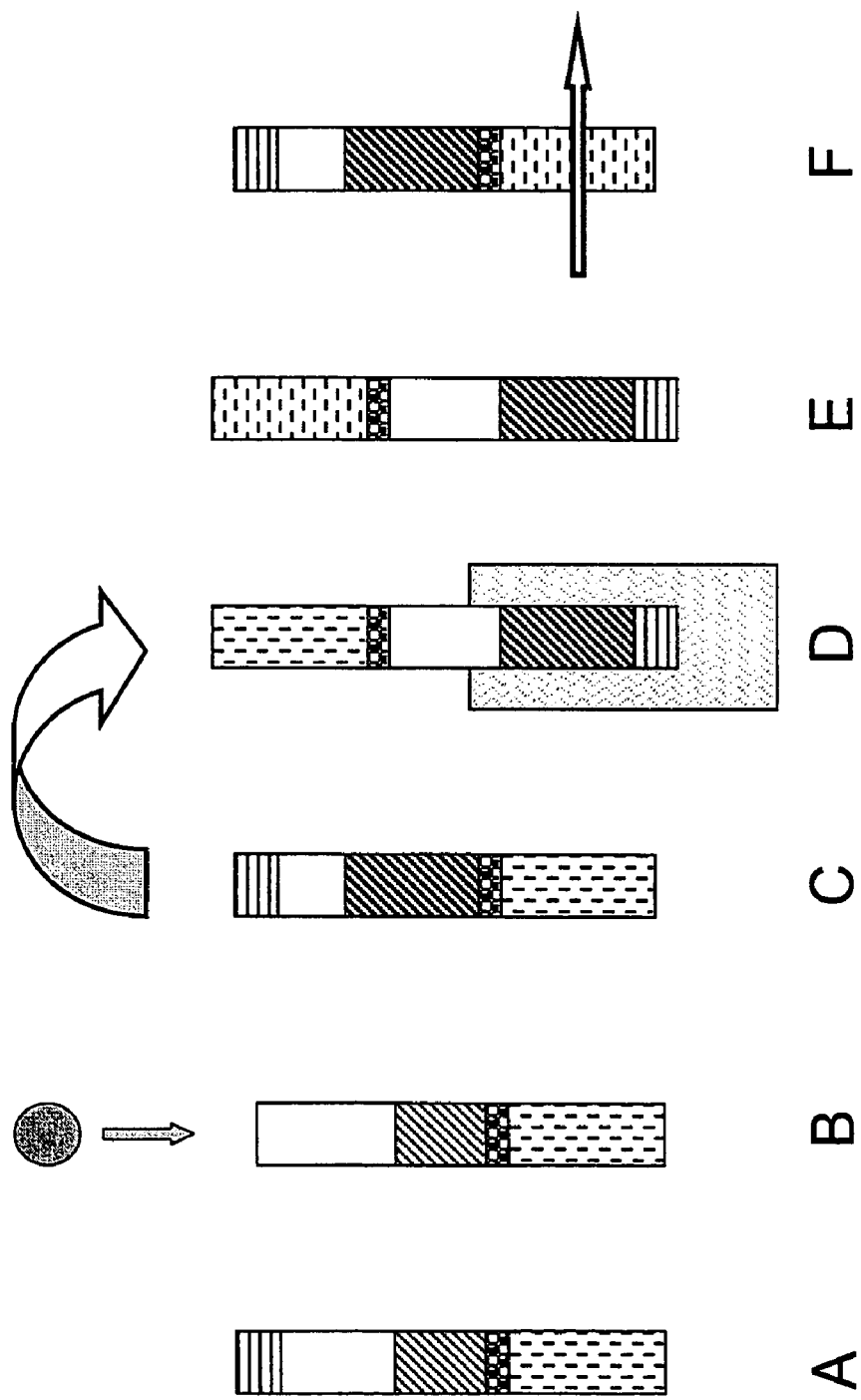
FIG. 3 depicts a diagram of the method according to the invention for the determination of volatile substances in solution.

FIG. 3 depicts a diagram of the method according to the invention for the determination of volatile substances in solution. The prefabricated cell (A) filled with indicator and digestion solution is briefly opened, and the sample is added (B). The cell is subsequently re-closed (C), inverted and, for example, introduced into a thermostat for the digestion (D). After completion of the digestion (E), the indicator solution can, after re-inversion of the container, be measured directly in a photometer (F).

Even without further comments, it is assumed that a person skilled in the art will be able to utilise the above description in its broadest scope. The preferred embodiments and examples should therefore merely be regarded as descriptive disclosure which is absolutely not limiting in any way.

The complete disclosure content of all applications, patents and publications mentioned above and below, in particular the corresponding application DE 101 21 999.7, filed on May 5, 2001, are incorporated into this application by way of reference.

EXAMPLES

1. Production of a Cell for TOC Determination
a) Hydrophobicisation

Example 1

Hydrophobicisation of the Glass Wall with a Silicone Layer

Since addition-crosslinking silicones do not exhibit good adhesion to the glass wall if they are added directly to the aqueous buffer solution, the glass wall is firstly hydrophobicised using commercial two-component silicone Kwik-Sil® from World Precision Instruments Inc. To this end, the two components of Kwik-Sil® are diluted 1:1% by volume with diethyl ether, the two solutions are combined, and the clear liquid is applied to the inner wall of the glass container at the level where the silicone membrane is to be polymerised in. By means of rotational movements along the longitudinal axis, a uniform thin ring is applied. After 1 minute, the ring is dry. In order to remove any solvent residues, the cell is stored in a drying cabinet at 60° C. for 2 hours.

Example 2

Hydrophobicisation of the Glass Wall with a Covalently Bonded, Carbon-Free Silane Layer 94 ml of ethanol, 1 ml of trimethoxysilane (T9895, ABCR GmbH & Co) and 4 ml of water are mixed. The pH is adjusted to from 4 to 5 using dilute $H_2SO_4$. 0.3 ml of this solution is pipetted into a vertical cell. The cell is placed in the drying cabinet at 140° C. for one hour. This gas-phase silanisation results in effective coupling of the silane to the glass wall and gives rise to a virtually unimolecular hydrophobic coating.

b) Filling of the Container with the Indicator Solution 4.5 ml of a Thymol Blue indicator solution (buffer concentration borate 3.5 mmol/l, pH 9.7, Thymol Blue 0.06 mmol/l) are introduced into the cell. The surface of the indicator solution is at the level of the silicone primer which has previously been polymerised in. The introduction of the indicator solution and the application of the membrane are carried out under nitrogen in order to reduce the ingress of carbon dioxide from the air. Due to the hydrophobicisation of the glass wall, a curved meniscus does not form on the water surface, meaning that the silicone membrane/glass wall contact area is significantly increased and the silicone membrane achieves a uniform layer thickness.

c) Introduction of the Silicone Membrane by Polymerisation 2.5 ml of base (DMS-V22, polydimethylsiloxane, vinyldimethyl-terminated, visc. 200 from ABCR GmbH & Co, Karlsruhe) and 0.1 ml of crosslinker (HMS-301, methylhydro-(65-70%) dimethylsiloxane copolymer from ABCR GmbH & Co, Karlsruhe) are mixed, and 2 µl of initiator (PCO-075 from ABCR GmbH & Co, Karlsruhe) are added to the clear solution with vigorous stirring. 0.5 ml of the silicone mixture is introduced dropwise onto the surface of the indicator solution. A clear silicone membrane with a thickness of about 2 mm forms. This membrane is solid after 10 minutes at room temperature. In order to complete the polymerisation, the cell is kept under nitrogen for a further 1 hour and then sealed.

2. TOC Analysis According to the Invention

A TOC test cell is constructed from the following components:

Two-component silicone for hydrophobicisation of the glass wall Name of the silicone: Kwik-Sil®, low viscosity silicone kit, marketed by World Precision Instruments, Inc.

Two-component silicone for the membrane DMS-V22, polydimethylsiloxane, vinyldimethyl-terminated, visc. 200, base HMS-301, methylhydro-(65-70%) dimethylsiloxane copolymer, crosslinker PCO-075, platinum/divinyltetramethyldisiloxane complex, 3% Pt, catalyst, marketed by ABCR GmbH & Co.

Hydrophobicisation of the Glass Wall

Each individual component of the Kwik-Sil® silicone is diluted 1:1% by volume with diethyl ether. The two solutions are combined, and the clear liquid mixture is applied to the inside of the glass bottle at the level where the silicone membrane is polymerised in. By means of rotational movements about the longitudinal axis of the glass bottle, a uniformly thin ring is applied. The solvent evaporates quickly, and the thin film is dry after 1 minute. The bottles are stored in a drying cabinet at 60° C. for 2 hours, during which all solvent residues are expelled from the very thin "primer".

Indicator 4.5 ml of the blue indicator solution with a buffer concentration of borate 3.5 mmol/l, pH 9.7, indicator concentration Thymol Blue 0.06 mmol/l, are introduced into the bottle. The surface of the indicator solution is at the level of the silicone "primer" which has previously been polymerised in. The introduction of the indicator and the application of the silicone membrane are carried out under nitrogen in order to reduce the ingress of carbon dioxide from the air.

Silicone membrane 2.5 ml of base (DMS-V22, polydimethylsiloxane, vinyldimethyl-terminated, visc. 200) and 0.1 ml of crosslinker (HMS-301, methylhydro-(65-70%) dimethylsiloxane copolymer) are mixed. 2 μl of initiator PCO-075 are added to the clear liquid solution with vigorous stirring. The processing time after addition of the initiator is a maximum of 5 minutes. 0.5 ml of the silicone mixture is introduced dropwise onto the surface of the indicator solution. A clear silicone membrane with a thickness of 2 mm forms. This membrane is solid after 15 minutes. The bottles are stored upright in a stream of nitrogen in order to complete the polymerisation and sealed using a screw cap after 2 hours.

Performance of the Experiment:

4.5 ml of solutions containing 25, 50, 100, 200 and 400 mg/l of carbon are pipetted into three of the TOC test cells described above. The cells are sealed using a screw cap and placed inverted in a thermostat (MERCK thermoreactor TR 200) at 100° C. After a digestion time of 2 hours, they are measured using the photometer (MERCK SQ 118).

The invention claimed is:

1. A method for the determination of a gaseous substance or a substance which can be converted into gas form in a sample comprising:
    a) opening a cell comprising at least two zones separated by an ion-impermeable, gas-permeable membrane which forms:
        i) a compartment for sample and optionally digestion solution and
        ii) a compartment containing an indicator solution, and wherein the cell can be sealed in a gas and liquid-tight manner by a closure,
    b) filling compartment (i) with the sample and optional digestion solutions,
    c) sealing the cell with the closure,
    d) inverting the cell and digesting the sample to produce liberated gas,
    e) re-inverting the cell after the sample is digested and
    f) measuring the indicator solution
    wherein steps a-f are consecutive.

2. A method according to claim 1, wherein al least one ion-impermeable, gas-permeable membrane consists of a silicone polymer.

3. A method according to claim 1, wherein at least one membrane has been clamped into the cell.

4. A method according to claim 1, wherein at least one membrane has been polymerised into the cell.

5. A method according to claim 1, wherein said membrane is hydrophobic.

6. A method according to claim 1, wherein said cell is made of glass or an organic polymer.

7. A method according to claim 1, wherein said cell is optically transparent or has a window of optically transparent material.

8. A method according to claim 1, wherein said cell is made of polycarbonate or quartz.

9. A method according to claim 1, wherein said cell fits into a commercial dry thermostat for digestion of said sample or can be inserted as a measurement container into a measuring instrument for detection.

10. A method according to claim 1, wherein said indicator solution can be measured by photometric, fluorimetric or nephelometric means.

11. A method according to claim 1, wherein said membrane is polytetrafluoroethylene.

12. A method according to claim 1, wherein the wails of said compartments are partly or fully hydrophobicized.

13. The method according to claim 1, wherein the total organic carbon content is determined.

14. A method for the determination of a gaseous substance or a substance which can be converted into gas form in a sample comprising:
    a) opening a cell that is divided by at least two ion-impermeable, gas-permeable membranes into at least three zones separated by the membranes, said zones comprising:
        i) a compartment for indicator solution which is filled with indicator solution,
        ii) a compartment for washing solutions which is filled with washing solution and
        iii) a compartment for sample and optionally digestion solutions,
    b) filling compartment (iii) with the sample and optional digestion solution,
    c) sealing the cell with said closure,
    d) inverting the cell and digesting the sample to produce liberated gas,
    e) re-inverting the cell after the sample is digested and
    f) measuring the indicator solution
    wherein said liberated as contacts said washing solution and
    wherein said step are consecutive.

15. The method according to claim 14, wherein the washing solution is lead (II) nitrate.

16. The method according to claim 14, wherein the total organic carbon content is determined.

* * * * *

UNITED STATES PATENT AND TRADEMARK OFFICE
CERTIFICATE OF CORRECTION

PATENT NO. : 7,390,673 B2 Page 1 of 1
APPLICATION NO. : 10/476639
DATED : June 24, 2008
INVENTOR(S) : Ingo Klimant It is certified that error appears in the above-identified patent and that said Letters Patent is hereby corrected as shown below:

Column 10, line 26, reads "wherein the wails" should read -- wherein the walls --

Column 10, line 52, reads "said step are" should read -- said steps are --

Signed and Sealed this

Seventeenth Day of February, 2009

JOHN DOLL
*Acting Director of the United States Patent and Trademark Office*